United States Patent
Yunoki et al.

(10) Patent No.: US 7,030,269 B2
(45) Date of Patent: Apr. 18, 2006

(54) CATALYST AND PROCESS FOR PRODUCTION OF ACRYLIC ACID

(75) Inventors: Hiromi Yunoki, Himeji (JP); Michio Tanimoto, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/684,285

(22) Filed: Oct. 13, 2003

(65) Prior Publication Data

US 2004/0092769 A1    May 13, 2004

(30) Foreign Application Priority Data

Nov. 12, 2002   (JP) ............................. 2002-328487

(51) Int. Cl.
*C07C 51/232* (2006.01)
(52) U.S. Cl. ...................................... 562/535; 562/532
(58) Field of Classification Search ............... 562/512, 562/523, 531, 532, 534, 535; 502/300, 305, 502/311, 312; 359/337.5
See application file for complete search history.

(56) References Cited

U.S. PATENT DOCUMENTS

| | | | | |
|---|---|---|---|---|
| 4,892,856 A | * | 1/1990 | Kawajiri et al. | ............ 502/247 |
| 5,959,143 A | * | 9/1999 | Sugi et al. | ................. 562/534 |

FOREIGN PATENT DOCUMENTS

| | | |
|---|---|---|
| CA | 2114681 A1 | 8/1994 |
| CA | 2163834 A1 | 5/1996 |
| EP | 0 758 562 A1 | 2/1997 |
| EP | 1 138 385 A1 | 10/2001 |
| JP | 5-96183 A | 4/1993 |
| JP | 6-279030 A | 10/1994 |
| JP | 8-10621 A | 1/1996 |
| JP | 8-252464 A | 10/1996 |
| JP | 8-299797 A | 11/1996 |
| JP | 2001-79408 A | 3/2001 |

* cited by examiner

*Primary Examiner*—Johann Richter
*Assistant Examiner*—Karl Puttlitz

(57) ABSTRACT

There are disclosed: a catalyst which can be used for production of acrylic acid and is excellent in the catalytic performances (e.g. conversion of starting material, selectivity of aimed product) and further has very high physical strength; and a process for production of acrylic acid using this catalyst. The above catalyst for production of acrylic acid is a catalyst which is obtained by a process including the steps of: heating a mixed liquid of starting materials including molybdenum and vanadium as essential components; and then molding the resultant dried material with a liquid binder; and then calcining the resultant molding; with the catalyst being characterized in that the liquid binder is an aqueous liquid of 7.0 to 10.0 in pH. The above process for production of acrylic acid is a process which comprises the step of carrying out catalytic gas phase oxidation of acrolein in the presence of molecular oxygen, thereby producing the acrylic acid; with the process being characterized by using the above catalyst for production of acrylic acid according to the present invention.

4 Claims, No Drawings

CATALYST AND PROCESS FOR PRODUCTION OF ACRYLIC ACID

BACKGROUND OF THE INVENTION

A. Technical Field

The present invention relates to: a catalyst used for production of acrylic acid; and a process for production of acrylic acid using this catalyst. Specifically, the present invention relates to: a catalyst for production of acrylic acid, wherein the catalyst is excellent in such as activity, selectivity, and physical strength; and a process for production of acrylic acid, wherein the process comprises the step of carrying out catalytic gas phase oxidation of acrolein in the presence of molecular oxygen in the presence of the above catalyst, thereby producing the acrylic acid.

B. Background Art

As a catalyst for efficiently producing acrylic acid by catalytic gas phase oxidation of acrolein (catalyst for production of acrylic acid), there is often used a catalyst which is obtained by a process including the steps of: for example, adding a liquid binder to a catalytic component powder obtained from a mixed liquid of starting materials including molybdenum and vanadium as essential components; and then molding the resultant mixture; and then calcining the resultant molding. As to processes for producing this catalyst, various proposals have been made.

Examples of these production processes include: (1) a process including the steps of evaporating a mixed liquid of starting materials to dryness, and then adding polyvinyl alcohol, a water-absorbent resin, and water to the resultant dried material, and then kneading the resultant mixture, and then extrusion-molding the kneaded mixture (for example, refer to JP-A-096183/1993); (2) a process including the steps of spraywise drying a mixed liquid of starting materials, and then calcining the resultant dried material at 400° C., and then supporting the resultant calcined structure onto a carrier using water as a binder with such as a rotating drum type supporting apparatus (for example, refer to JP-A-279030/1994); (3) a process including the steps of drying a mixed liquid of starting materials by any method of evaporation to dryness, spray drying, drum drying, and gas flow drying, and then adding propyl alcohol and water to the resultant dried material to mix them together, and then extrusion-molding the resultant mixture (for example, refer to JP-A-010621/1996); (4) a process including the steps of spraywise drying a mixed liquid of starting materials and then calcining the resultant dried material at 400° C., and then supporting the resultant calcined structure onto a carrier using a liquid binder including water and an organic compound having a boiling point or sublimation temperature of higher than 100° C. under normal pressure (for example, refer to JP-A-252464/1996); and (5) a process including the steps of drying a mixed liquid of starting materials, and then calcining the resultant dried material in the range of 250 to 500° C., and then supporting the resultant calcined structure onto a carrier using such as an aqueous glycerol solution as a binder with a tumbling granulator (for example, refer to JP-A-299797/1996 and JP-A-079408/2001).

The above liquid binder is used for the purpose of such as 1) to 4) below. 1) Providing the catalytic component powder with moderate viscosity and flowability, thereby reducing the friction force between a molding machine and the catalytic component powder and/or between particles of the catalytic component powder during the molding; 2) intending to enhance the moldability such as the molding speed, the uniformity of the molded shape, the yield, and the workability (handling ability); 3) intending to enhance the binding force between particles of the catalytic component powder (this leads also to the enhancement of the physical strength of the catalyst) and, in the case of obtaining the supported catalyst, intending to promote and strengthen the binding and fixation between the carrier and the catalytic component powder; or 4) forming pores in the catalyst by utilizing the removal of the binder from the molding due to heating (e.g. calcining) after the molding.

However, all the catalysts for production of acrylic acid, which are obtained by the above prior processes, are still insufficient as to: the catalytic performances such as catalytic activity; and the physical strength of the catalysts themselves.

SUMMARY OF THE INVENTION

A. Object of the Invention

Thus, an object of the present invention is to provide: a catalyst which can be used for production of acrylic acid and is excellent in the catalytic performances (e.g. conversion of starting material, selectivity of aimed product) and further has very high physical strength; and a process for production of acrylic acid using this catalyst.

B. Disclosure of the Invention

In the process of diligent study to solve the above-mentioned problems, the present inventors directed their attention to a liquid binder which is used such as by being added to a dried material from a mixed liquid of starting materials in preparation for molding this dried material with a molding machine such as an extrusion-molding machine or a tumbling granulator.

As a result, the present inventors have found out that a catalyst for production of acrylic acid, which is obtained using an aqueous liquid satisfying a specific range of pH value as the above liquid binder, could solve the above-mentioned problems at a stroke. And then the present inventors have completed the present invention by also confirming that the acrylic acid can efficiently be obtained as a result of actually using the above catalyst in the catalytic gas phase oxidation of such as acrolein.

That is to say, a catalyst for production of acrylic acid, according to the present invention, is a catalyst which is obtained by a process including the steps of: heating a mixed liquid of starting materials including molybdenum and vanadium as essential components; and then molding the resultant dried material with a liquid binder; and then calcining the resultant molding; with the catalyst being characterized in that the liquid binder is an aqueous liquid of 7.0 to 10.0 in pH.

In addition, a process for production of acrylic acid, according to the present invention, is a process which comprises the step of carrying out catalytic gas phase oxidation of acrolein in the presence of molecular oxygen, thereby producing the acrylic acid; with the process being characterized by using the above catalyst for production of acrylic acid according to the present invention.

These and other objects and the advantages of the present invention will be more fully apparent from the following detailed disclosure.

DETAILED DESCRIPTION OF THE INVENTION

Hereinafter, detailed descriptions are given about the catalyst for production of acrylic acid according to the present invention and the process for production of acrylic acid using this catalyst. However, the scope of the present invention is not bound to these descriptions. And other than the following illustrations can also be carried out in the form of appropriate modifications of the following illustrations within the scope not departing from the spirit of the present invention.

The catalyst for production of acrylic acid, according to the present invention, is obtained by a process including: (1) the step of heating a mixed liquid (which is in a state of an aqueous solution or slurry) of starting materials including molybdenum and vanadium as essential components, thereby obtaining a dried material; (2) the step of molding this dried material with a liquid binder; and (3) the step of calcining the resultant molding. In the above step (2), an aqueous liquid of 7.0 to 10.0 in pH is used as the liquid binder.

The catalyst for production of acrylic acid, according to the present invention, is a catalyst comprising an oxide and/or a composite oxide which include molybdenum and vanadium as essential metal elements. This catalyst may be any catalyst if it enables the production of acrylic acid from acrolein by its catalytic gas phase oxidation reaction. However, it is favorable that the oxide and/or the composite oxide, which include molybdenum and vanadium as essential metal elements, is an oxide and/or a composite oxide which have a metal element composition as shown by a general formula (1) below:

$$Mo_a V_b A_c B_d C_e O_x \quad (1)$$

(where: Mo is molybdenum; V is vanadium; A is niobium and/or tungsten; B is at least one element selected from the group consisting of chromium, manganese, iron, cobalt, nickel, copper, zinc, and bismuth; C is at least one element selected from the group consisting of phosphorus, tin, antimony, and tellurium; and O is oxygen; and further, a, b, c, d, e, and x denote atomic ratios of Mo, V, A, B, C, and O respectively; and, when a=12, the following inequalities are satisfied: $1 \leq b \leq 14$; $0 < c \leq 12$; $0 < d \leq 10$; and $0 \leq e \leq 10$; and x is a numerical value as determined by the oxidation state of each element).

There is no especial limitation on the starting materials for obtaining the above oxide and/or composite oxide which include molybdenum and vanadium as essential metal elements. Ammonium salts, nitrates, carbonates, chlorides, sulfates, hydroxides, organic acid salts, and oxides of metal elements as generally used for this kind of catalyst, or a mixture of these, may be used in combination of at least two of them. However, the ammonium salts and nitrates are favorably used.

The mixed liquid of the above starting materials (starting-materials-mixed liquid) may be prepared by processes as generally used for production of this kind of catalyst. For example, the above starting materials are mixed into water in order, thereby forming an aqueous solution or slurry. In the case where at least two aqueous solutions or slurries are prepared according to the kinds of the starting materials, these aqueous solutions or slurries may be mixed together in order. There is no especial limitation on the conditions for the above mixing (e.g. mixing order, temperature, pressure, and pH). The mixed liquid of starting materials, as obtained in this way, is heated to thereby form the dried material. There is no especial limitation on the heating method for obtaining this dried material and on the form of this dried material. For example, a powdery dried material may be obtained with such as a spray dryer and a drum dryer, or a blockish or flaky dried material may be obtained by heating under a gas stream with such as a box-type dryer or a tunnel-type dryer. In addition, the resultant dried material may be either a product obtained merely by drying the mixed liquid of starting materials as it is (this product contains volatiles due to such as decomposition of various salts in the case where further heat-treated at high temperature), or a calcined product obtained by heat-treating at least a portion of the mixed liquid of starting materials at high temperature (this product does not contain any volatiles due to such as decomposition of various salts). Thus, there is no especial limitation. However, the former is preferable.

The resultant dried material is transferred to the subsequent molding step after having, if necessary, been subjected to a pulverization step and/or a classification step for obtaining a powder having appropriate particle diameters.

In the molding step, the resultant dried material is molded with the liquid binder. Specifically, there can be adopted such as: a method including the steps of adding the liquid binder to the resultant dried material to mix them together and then molding the resultant mixture; or, in the case of supporting the resultant dried material onto a desired carrier (obtaining a supported catalyst), a method including the steps of wetting the above carrier with the liquid binder and then adding the dried material to the wetted carrier to thereby support the dried material onto the carrier.

In the present invention, it is important that the aqueous liquid of 7.0 to 10.0 in pH is used as the liquid binder which is used when the dried material is molded. The pH of the above binder is more favorably in the range of 7.5 to 9.5, still more favorably 8.0 to 9.0. Incidentally, in the present invention and herein, the pH of the liquid binder all refers to its value in a state of 25° C.

In the case where the pH of the above liquid binder is less than 7.0, the resultant catalyst for production of acrylic acid has the following possibilities: the catalytic performances (e.g. conversion of starting material, selectivity of aimed product), particularly the selectivity of acrylic acid, may be much inferior; and the yield of the aimed product may also greatly be deteriorated; and the physical strength of the catalyst may also be low; and further, in the process for producing the catalyst, the moldability of the dried material may be so inferior as to merely give a molded product of the warped shape and therefore as to be unable to obtain a catalyst of the desired shape; and besides, for example, in the case where the molding is carried out with an extrusion-molding machine, when the dried material is compressed, the viscosity may increase more than is necessary, so that the molding speed may greatly be slowed and, in the worst case, the molding may become impossible. In addition, in the case where the molding is carried out with a tumbling granulator, there are the following possibilities: the viscosity of the dried material may increase during the granulating motion so much as to cause cohesion of the granulated particles. Furthermore, in the case where the supported catalyst is obtained, the dried material may adhere to the inner surface of a supporting treatment vessel in such a large amount as to deteriorate the yield. On the other hand, in the case where the pH of the above liquid binder is higher than 10.0, the resultant catalyst for production of acrylic acid has the following possibilities: the catalytic performances (e.g. conversion of starting material, selectivity of aimed product) may be inferior; and the yield of the aimed product may also greatly be deteriorated; and besides, according to circumstances (for example, according to the kinds of the starting materials for the catalyst and the kind of the liquid binder), the cohesive strength of the dried material may be so weak as to be unable to obtain sufficient physical strength.

If the liquid binder of which the pH value (25° C.) satisfies the above range is used, then there can always stably be obtained the catalyst for production of acrylic acid having very high physical strength, and besides, there can be obtained the catalyst which can display high performance also in both catalytic performances of the conversion of acrolein and the selectivity of acrylic acid. In addition, surprisingly, as to the yield of acrylic acid as determined from the values of the above conversion and selectivity, there can be obtained the catalyst which can always stably display such levels as cannot possibly be attained when conventional liquid binders represented by such as ion-exchanged water are used. Specifically, if the above catalyst for production of acrylic acid is obtained using the above specific liquid binder, then there can always stably be obtained the catalyst which can display very high levels as to all functions and performances of the physical strength, the conversion of acrolein, the selectivity of acrylic acid, and the yield of acrylic acid.

There is no especial limitation on the liquid binder which satisfies the above specific range of pH value and can be used in the present invention. However, specific examples thereof include: dilute ammonia water; aqueous solutions containing various ammonium salts; and aqueous solutions containing various organic compounds. As to these, even if they are materials which can come in a state not satisfying the above specific range of pH value in nature, it is enough that their pH values are adjusted in the above specific range in advance of the use for the present invention. In addition, generally, water (e.g. ion-exchanged water) is also used as the liquid binder. However, in the usual handling, even the ion-exchanged water exists in a state having absorbed carbon dioxide gas from air. Therefore, its pH is not 7.0, but in the weak acid range less than it.

Examples of usable ammonium salts in the above aqueous solutions containing the ammonium salts include ammonium carbonate, ammonium hydrogencarbonate, ammonium sulfate, ammonium hydrogensulfate, ammonium nitrate, and ammonium citrate. Above all, ammonium carbonate and ammonium nitrate are preferable.

Examples of usable organic compounds in the above aqueous solutions containing the organic compounds include ethanolamine, pyridine, and ethylamine. In addition, even such organic compounds as are inherently nonbasic ones (e.g. alcohols such as methanol, ethanol, propanol, and isopropanol, and glycerol) can be used, for example, by adding such as ammonia water to an aqueous ethanol solution to adjust the pH value so as to satisfy the above specific range.

In the present invention, the above liquid binder may be a binder including various ammonium radicals. The various ammonium salts which are supply sources of the various ammonium radicals are occasionally used also as starting materials, but are easy to remove by heat-treatment and little exercise bad influence on the finally obtained catalyst for production of acrylic acid.

The amount of the liquid binder as added to the dried material to mix them together (amount as added) is not especially limited, but may be set appropriately for the adopted molding method. In the case where the above amount as added is too large, there is a possibility that the moldability of the dried material may be deteriorated to such a degree that the molding cannot be carried out. In the case where the above amount as added is too small, there is a possibility that: the cohesion of the dried material may be so weak that the physical strength of the catalyst is low or that the molding itself cannot be carried out. In the case where the molding is carried out by the extrusion-molding, there is a possibility that a molding machine may be broken if things come to the worst.

The above liquid binder (aqueous liquid satisfying the above specific range of pH value) is usable also in the form as obtained by adding thereto aqueous solutions of various substances and/or the various substances alone to mix them together. Examples of the above various substances include: molding assistants for enhancing the moldability; reinforcements and binders for enhancing the catalyst strength; and substances that are generally used as pore-forming agents for forming pores in the catalyst. Preferable of these substances are substances that do not have bad influence on the catalytic performances (e.g.: activity; selectivity of aimed product) by the addition of these substances. Specifically, the preferable substances are, for example, as follows: (1) substances that do not remain in the catalyst after the calcination; and (2) substances that do not have bad influence on the catalytic performances even if they remain in the catalyst after the calcination.

Specific examples of the above (1) include: starch, cellulose, and melamine cyanurate.

Specific examples of the above (2) include those which are generally known as the reinforcements, such as silica, alumina, glass fibers, silicon carbide, and silicon nitride. In the present invention, the catalyst as produced has practically sufficient physical strength, but the above reinforcements are added thereto when the still higher physical strength is necessary.

In the case where the amount of the above various substances as added is in excess, the physical strength of the catalyst is occasionally remarkably lowered. Therefore it is favorable to add them in such an amount as does not lower the physical strength of the catalyst to such an extent that the catalyst cannot be practically used as an industrial catalyst.

The catalyst for production of acrylic acid, according to the present invention, may be either a molded catalyst as obtained by molding the dried material into a definite shape, or a supported catalyst as obtained by molding the dried material by supporting the dried material onto any inert carrier having a definite shape, for example, a particulate carrier. Usable examples of the above inert carrier include alumina, silica, silica-alumina, titania, magnesia, steatite, and silicon carbide.

In the case of the supported catalyst, the supporting ratio is favorably in the range of 10 to 70 mass %, more favorably 15 to 50 mass %.

As to the molding method adoptable in the molding step, prior publicly known methods and means may be used. Applicable are, for example, molding methods such as extrusion-molding methods (extrusion-molding machines), granulation methods (tumbling granulators and centrifugal-flow-coating apparatuses), and Marumerizer methods.

The shape of the catalyst for production of acrylic acid, according to the present invention, is not especially limited. For example, any shape such as a column shape, a ring shape, a spherical shape, and an irregular shape can be selected.

The average diameter of the catalyst for production of acrylic acid, according to the present invention, is in the range of 1 to 15 mm, favorably 3 to 10 mm.

The catalyst for production of acrylic acid, according to the present invention, is obtained by a process including the steps of: molding the dried material with the liquid binder; and then calcining the resultant molding, favorably in the temperature range of 350 to 450° C. (more favorably 380 to 420° C.), for about 1 to about 10 hours. Before being calcined, the above molding may be heat-treated at a temperature lower than the calcination temperature.

The process for production of acrylic acid, according to the present invention, is a process which comprises the step of carrying out catalytic gas phase oxidation of acrolein in the presence of molecular oxygen, thereby producing the acrylic acid; with the process being characterized by using the above catalyst for production of acrylic acid according to the present invention.

Except for using the present invention catalyst as a catalyst, there is no especial limitation on the process which comprises the step of carrying out catalytic gas phase oxidation of acrolein, thereby producing the acrylic acid. This production process can be carried out with generally used apparatuses, by generally used methods, and under generally used conditions.

The above acrolein is subjected to the catalytic gas phase oxidation generally in a state of a raw gas containing this acrolein. As such a raw gas, a mixed gas containing acrolein as obtained by direct oxidation of propylene is also usable after air or oxygen and further water vapor and/or another gas have been added thereto if necessary, needless to say a mixed gas including acrolein, oxygen, and an inert gas. By-products as contained in the mixed gas containing acrolein as obtained by direct oxidation of propylene, such as acrylic acid, acetic acid, carbon oxide, propane, or unreacted propylene, do no harm upon the catalyst for production of acrylic acid as used in the present invention.

The catalytic gas phase oxidation reaction in the present invention may be carried out either by a one-pass method or recycling method. Such as fixed-bed reactors, fluidized-bed reactors, and moving-bed reactors can be used as reactors.

As to conditions of the above reaction, it is possible to adopt conditions as conventionally used for the production of acrylic acid by the catalytic gas phase oxidation reaction. For example, the reaction may be carried out by bringing a mixed gas into contact with the above catalyst for production of acrylic acid according to the present invention in the temperature range of 200 to 400° C. (favorably 220 to 380° C.) under a pressure of 0.1 to 1 MPa at a space velocity of 300 to 10,000 hr$^{-1}$ (STP) (favorably 500 to 5,000 hr$^{-1}$ (STP)), wherein the mixed gas includes acrolein 1 to 15 volume % (favorably 4 to 12 volume %), oxygen 0.5 to 25 volume % (favorably 2 to 20 volume %), water vapor 0 to 30 volume % (favorably 0 to 25 volume %), and an inert gas (e.g. nitrogen) 20 to 80 volume % (favorably 50 to 70 volume %).

(Effects and Advantages of the Invention):

The present invention can provide: a catalyst which can be used for production of acrylic acid and is excellent in the catalytic performances such as catalytic activity (namely, conversion of starting material, selectivity of aimed product) and also can stably enhance the yield of the aimed product and further always has very high physical strength; and a process for production of acrylic acid using this catalyst.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to them in any way. Incidentally, for convenience, the unit "part(s) by mass" may hereinafter be abbreviated simply to "part(s)".

The details of various measurement and calculation methods in the following Examples and Comparative Examples are shown below.

<Method for Measurement of Catalyst Strength>:

A stainless-steel-made reaction tube of 25 mm in inner diameter and 5,000 mm in length is set in a vertical direction, and the lower end of this reaction tube is closed with a stainless-steel-made receiving plate of 1 mm in thickness.

Next, about 50 g of catalyst is dropped from the upper end of the reaction tube into the reaction tube, and then the stainless-steel-made receiving plate as placed at the lower end of the reaction tube is removed to gently extract the catalyst from the reaction tube. The catalyst as extracted is sieved with a sieve having a mesh opening size of 4 mm. The catalyst strength was evaluated from the following equation. The higher numerical value refers to the higher catalyst strength.

Catalyst strength (mass %)=[(mass of catalyst remaining on sieve)/(mass of catalyst as dropped from upper end of reaction tube)]×100

<Method for Calculation of Supporting Ratio>:

Supporting ratio (mass %)=(mass of catalyst obtained−mass of carrier used)÷mass of catalyst obtained×100

<Conversion of Acrolein>:

Conversion of acrolein (mol %)=(mols of reacted acrolein/mols of supplied acrolein)×100

<Yield of Acrylic Acid>:

Yield of acrylic acid (mol %)=(mols of produced acrylic acid/mols of supplied acrolein)×100

<Selectivity of Acrylic Acid>:

Selectivity of acrylic acid (mol %)=(mols of produced acrylic acid/mols of reacted acrolein)×100

EXAMPLE 1

(Preparation of Catalyst):

While 20,000 parts of pure water was heat-mixed, 3,000 parts of ammonium molybdate, 994 parts of ammonium metavanadate, and 574 parts of ammonium paratungstate were dissolved thereinto. Separately, while 2,000 parts of pure water was heat-mixed, 958 parts of copper nitrate trihydrate was dissolved thereinto. The resultant two aqueous solutions were mixed together, and then the resultant mixture was dried with a drum dryer and then pulverized into the size of not larger than 500 μm, thus obtaining a powdery dried material.

A liquid binder of pH 7.3 (25° C.) was prepared by mixing 25% ammonia water and ion-exchanged water together. Incidentally, as the ion-exchanged water, there was used that having a conductivity of 0.1 μS/cm at 25° C. (the same in all the following Examples and Comparative Examples).

Onto a rotating dish of a tumbling granulator, there was placed a silica-alumina carrier having diameters of 4.5 to 5.0 mm. While the rotating dish was rotated at 15 rpm in a state tilted at 30° to the horizontal plane, the liquid binder was sprayed. After this treatment had been carried out for 10 minutes, the powdery dried material was added to support it onto the carrier. Next, the resultant product was got out and then calcined at 400° C. under air atmosphere for 6 hours, thus obtaining a catalyst (1). The metal element composition of this catalyst (1) except for oxygen was shown below. In addition, the supporting ratio in the catalyst (1) was 20.3 mass %.

$$Mo_{12}V_{6.0}W_{1.5}Cu_{2.8} \qquad \text{Catalyst (1)}$$

(Oxidation Reaction):

An amount of 1,000 milliliters of the catalyst (1) was packed into a stainless-steel-made reaction tube of 25 mm in diameter, and then an oxidation reaction was carried out at a reaction temperature of 220° C. at a space velocity of 1,800 $h^{-1}$ (STP) by introducing a mixed gas including acrolein 4 volume %, oxygen 5 volume %, water vapor 40 volume %, and nitrogen 51 volume %. The results about the conversion of acrolein, the selectivity of acrylic acid, and the yield of acrylic acid are listed in Table 1.

EXAMPLES 2 TO 4

(Preparation of Catalysts):

Each of catalysts (2) to (4) was obtained in the same way as of Example 1 except that the mixing ratio of the 25% ammonia water and the ion-exchanged water was changed to change the pH of the liquid binder as used. The metal element compositions of the catalysts (2) to (4) except for oxygen were the same as of the catalyst (1).

In Table 1, there are listed: the pH of the liquid binder as used in the preparation of each of the catalysts (2) to (4); and the supporting ratio in each of the catalysts (2) to (4).

(Oxidation Reactions):

Each oxidation reaction was carried out in the same way as of Example 1 except that the catalyst (1) was replaced with each of the catalysts (2) to (4). The results about the conversion of acrolein, the selectivity of acrylic acid, and the yield of acrylic acid are listed in Table 1.

EXAMPLES 5 AND 6

(Preparation of Catalysts):

Catalysts (5) and (6) were obtained in the same way as of Example 1 except that the liquid binders as used were prepared by mixing a 50 mass % aqueous ammonium nitrate solution (as prepared by dissolving ammonium nitrate into ion-exchanged water) and 25% ammonia water together and then adjusting the pH at 25° C. of the resultant mixture to pH 7.7 and pH 9.3 respectively. The metal element compositions of the catalysts (5) and (6) except for oxygen were the same as of the catalyst (1).

In Table 1, there are listed: the pH of the liquid binder as used in the preparation of each of the catalysts (5) and (6); and the supporting ratio in each of the catalysts (5) and (6).

(Oxidation Reactions):

Each oxidation reaction was carried out in the same way as of Example 1 except that the catalyst (1) was replaced with each of the catalysts (5) and (6). The results about the conversion of acrolein, the selectivity of acrylic acid, and the yield of acrylic acid are listed in Table 1.

COMPARATIVE EXAMPLES 1 AND 2

(Preparation of Catalysts):

Each of catalysts (c1) and (c2) was obtained in the same way as of Examples 5 and 6 except that the liquid binders as used were prepared by changing the mixing ratio of the 50 mass % aqueous ammonium nitrate solution (as prepared by dissolving ammonium nitrate into ion-exchanged water) and the 25% ammonia water to change the pH at 25° C. of the resultant mixture. The metal element compositions of the catalysts (c1) and (c2) except for oxygen were the same as of the catalyst (1).

In Table 1, there are listed: the pH of the liquid binder as used in the preparation of each of the catalysts (c1) and (c2); and the supporting ratio in each of the catalysts (c1) and (c2).

(Oxidation Reactions):

Each oxidation reaction was carried out in the same way as of Example 1 except that the catalyst (1) was replaced with each of the catalysts (c1) and (c2). The results about the conversion of acrolein, the selectivity of acrylic acid, and the yield of acrylic acid are listed in Table 1.

COMPARATIVE EXAMPLE 3

(Preparation of Catalyst):

Catalyst (c3) was obtained in the same way as of Example 1 except that only the ion-exchanged water of pH 6.0 was used as the liquid binder. The metal element composition of the catalyst (c3) except for oxygen was the same as of the catalyst (1).

The supporting ratio in the catalyst (c3) was 20.2 mass %.

(Oxidation Reaction):

An oxidation reaction was carried out in the same way as of Example 1 except that the catalyst (1) was replaced with the catalyst (c3). The results about the conversion of acrolein, the selectivity of acrylic acid, and the yield of acrylic acid are listed in Table 1.

COMPARATIVE EXAMPLES 4 AND 5

(Preparation of Catalysts):

Catalyst (c4) of Comparative Example 4 was obtained in the same way as of Example 1 except that a 50 mass % aqueous ammonium nitrate solution (as prepared by dissolving ammonium nitrate into ion-exchanged water) was used as the liquid binder. The metal element composition of the catalyst (c4) except for oxygen was the same as of the catalyst (1).

In addition, catalyst (c5) of Comparative Example 5 was obtained in the same way as of Example 1 except that an aqueous nitric acid solution (as prepared by mixing concentrated nitric acid and ion-exchanged water together) was used as the liquid binder. The metal element composition of the catalyst (c5) except for oxygen was the same as of the catalyst (1).

In Table 1, there are listed: the pH of the liquid binder as used in the preparation of each of the catalysts (c4) and (c5); and the supporting ratio in each of the catalysts (c4) and (c5).

(Oxidation Reactions):

Each oxidation reaction was carried out in the same way as of Example 1 except that the catalyst (1) was replaced with each of the catalysts (c4) and (c5). The results about the conversion of acrolein, the selectivity of acrylic acid, and the yield of acrylic acid are listed in Table 1.

TABLE 1

| | Catalyst | Binder Kind | Binder pH (25° C.) | Supporting ratio (mass %) | Physical strength (mass %) | Conversion of acrolein (mol %) | Selectivity of acrylic acid (mol %) | Yield of acrylic acid (mol %) |
|---|---|---|---|---|---|---|---|---|
| Example 1 | (1) | Ammonia water | 7.3 | 20.3 | 98.6 | 98.7 | 95.7 | 94.5 |
| Example 2 | (2) | Ammonia water | 8.5 | 20.1 | 99.1 | 99.4 | 95.6 | 95.0 |
| Example 3 | (3) | Ammonia water | 8.9 | 20.0 | 99.0 | 99.3 | 95.6 | 94.9 |
| Example 4 | (4) | Ammonia water | 9.7 | 20.0 | 98.8 | 98.6 | 95.8 | 94.5 |
| Example 5 | (5) | Aqueous ammonium nitrate solution + Ammonia water | 7.7 | 20.0 | 99.0 | 99.0 | 95.7 | 94.7 |
| Example 6 | (6) | Aqueous ammonium nitrate solution + Ammonia water | 9.3 | 20.2 | 99.1 | 99.1 | 95.4 | 94.5 |
| Comparative Example 1 | (c1) | Aqueous ammonium nitrate solution + Ammonia water | 10.8 | 20.0 | 97.5 | 97.4 | 94.5 | 92.0 |
| Comparative Example 2 | (c2) | Aqueous ammonium nitrate solution + Ammonia water | 12.3 | 20.1 | 97.4 | 96.2 | 95.0 | 91.4 |
| Comparative Example 3 | (c3) | Ion-exchanged water | 6.0 | 20.2 | 97.1 | 98.7 | 94.7 | 93.5 |
| Comparative Example 4 | (c4) | Aqueous ammonium nitrate solution | 4.4 | 20.3 | 96.6 | 98.6 | 94.5 | 93.2 |
| Comparative Example 5 | (c5) | Aqueous nitric acid solution | 3.0 | 20.1 | 96.3 | 98.4 | 94.4 | 92.9 |

From the results shown in Table 1, it is possible to say that all the catalysts (catalysts (1) to (6)), as obtained in the Examples according to the present invention, have very high physical strength, and besides, indicate very high values also in both performances of the conversion of acrolein and the selectivity of acrylic acid, and are therefore extremely excellent catalysts. Furthermore, as to the yield of acrylic acid, all the catalysts (1) to (6) have provided the results superior to such levels as are not achieved by any of the catalysts (catalysts (c1) to (c5)) as obtained using the liquid binders which do not satisfy the specific range of pH value (25° C.) (liquid binders such as ion-exchanged water). This point can be said to be functions and effects such that all the above functions and performances of the physical strength, the conversion of acrolein, the selectivity of acrylic acid, and the yield of acrylic acid are on high levels. In addition, the above point can be said to be remarkable functions and effects of the catalysts (1) to (6) in comparison with the catalysts (c1) to (c5).

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for production of acrylic acid, which comprises the step of carrying out catalytic gas phase oxidation of acrolein in the presence of molecular oxygen, thereby producing the acrylic acid;
   with the step of carrying out catalytic gas phase oxidation using a catalyst which is obtained by a process that includes the steps of: heating a mixed liquid of starting materials including molybdenum and vanadium as essential components; and then molding the resultant dried material with a liquid binder; and then calcining the resultant molding; wherein the liquid binder is an aqueous liquid of 7.0 to 10.0 in pH.

2. A process for production of acrylic acid according to claim 1, wherein the liquid binder is an aqueous liquid of 7.5 to 9.5 in pH.

3. A process for production of acrylic acid according to claim 1, wherein a physical strength of the catalyst is 98.6 mass % or more.

4. A process for production of acrylic acid according to claim 3, wherein the physical strength of the catalyst is measured in accordance with the following procedure:
  a) providing a stainless-steel-made reaction tube of 25 mm in inner diameter and 5,000 mm in length and setting said stainless-steel-made reaction tube in a vertical direction;
  b) closing a lower end of said stainless-steel-made reaction tube with a stainless-steel-made receiving plate of 1 mm in thickness;
  c) dropping 50 g of the catalyst from an upper end of the stainless-steel-made reaction tube into the stainless-steel-made reaction tube;
  d) removing the stainless-steel-made receiving plate, having the catalyst that has been dropped, from the stainless-steel-made reaction tube such that the catalyst is extracted from the stainless-steel-made reaction tube;
  e) sieving the catalyst that has been extracted with a sieve having a mesh opening size of 4 mm; and
  f) wherein the physical strength (mass %) of the catalyst equals [(mass of catalyst remaining on sieve)/(mass of catalyst as dropped from the upper end of the stainless-steel-made reaction tube)]×100.

* * * * *